United States Patent [19]

Rajamannan

[11] Patent Number: 5,668,184
[45] Date of Patent: Sep. 16, 1997

[54] METHOD OF CONTROLLING SOIL AND PLANT PESTS WITH A NAPHTHALENE CONTAINING COMPOSITION

[76] Inventor: A. H. J. Rajamannan, 2120 Argonne Dr., Minneapolis, Minn. 55421

[21] Appl. No.: 709,362

[22] Filed: Sep. 6, 1996

[51] Int. Cl.$^6$ .......................... A01N 27/00; A01N 25/08; A01N 25/28; A01N 25/34
[52] U.S. Cl. .................. 514/765; 514/918; 514/919; 514/962; 514/963; 424/408; 424/409; 424/411; 424/413; 424/414; 424/DIG. 10
[58] Field of Search ...................... 514/765, 918, 514/919, 962, 963; 424/405, 408, 409, 411, 413, 414, DIG. 5, DIG. 10

[56] References Cited

U.S. PATENT DOCUMENTS

| | | | |
|---|---|---|---|
| 4,936,901 | 6/1990 | Surgant, Sr. et al. | 504/133 |
| 5,231,070 | 7/1993 | Narayanan et al. | 504/113 |
| 5,547,918 | 8/1996 | Newton et al. | 504/116 |

*Primary Examiner*—John Pak
*Attorney, Agent, or Firm*—Herman H. Bains

[57] ABSTRACT

A method of repelling soil borne pests, nematodes, insects and insect larvae includes applying a solution of naphthalene or precipitated flocculent naphthalene into or upon the soil where the naphthalene volatilizes and repels nematodes and soil pathogens. In another embodiment of the invention, micron size particles of naphthalene are encapsulated in a polymer which is injected into or applied to the surface of the soil. In a further embodiment of the invention, micron-sized particles of naphthalene are attached to a carrier strip which is applied to the surface of the soil as a mulch, applied below the surface of the soil, or attached to trees or plants for repelling pests.

2 Claims, No Drawings

METHOD OF CONTROLLING SOIL AND PLANT PESTS WITH A NAPHTHALENE CONTAINING COMPOSITION

FIELD OF THE INVENTION

This invention relates to a method of repelling pests that are harmful to crops, plants and trees.

BACKGROUND OF THE INVENTION

Nematodes and other soil pathogens can be extremely harmful to crop production. Various kinds of insects and insect larvae are harmful to trees, fruit and growing plants. Currently, fumigants such as methylbromide, which are used to control soil pathogens, are being phased out because they are harmful to the environment. Benign alternatives are being sought by the agricultural industry.

SUMMARY OF THE INVENTION

An object of this invention is to provide a method of controlling and repelling plant and crop pest by applying a naphthalene containing material to the soil, plants or trees and allowing the naphthalene to volatilize to repel the pest.

A more specific object of this invention is to provide a method of repelling soil borne pests including nematodes by injecting a solution containing naphthalene into the soil, the naphthalene first precipitating and then volatilizing into the soil to repel soil borne pathogens.

Another object of this invention is a method of repelling agricultural pests with naphthalene flocculates encapsulated in a polymer which is injected into the soil so as to release naphthalene vapors over a pre-determined period of time to repel pests such as nematodes.

In one embodiment of the invention, naphthalene is dissolved in a solvent, such as alcohol, and the solution is injected into the ground resulting in the precipitation of the naphthalene which thereafter volatilizes over a period of time to repel nematodes and other pathogenic organisms. In another embodiment of the invention, the naphthalene is partially solubilized and thereafter precipitated in an aqueous solution to produce a fine flocculent state which is injected into the soil. In a further embodiment, naphthalene flocculates are also micro-encapsulated in suitable polymers and the encapsulated flocculates are injected into the soil which results in a relatively slow release of the naphthalene vapors over a longer period of time. In a further embodiment of the invention, the naphthalene flocculates are incorporated into plastic or paper bags or strips which are then positioned below or upon the surface of the soil to repel nematodes and pests. The strips may also be attached or applied to trees or plants for repelling insects or insect larvae.

DESCRIPTION OF THE PREFERRED EMBODIMENT

Naphthalene, $C_{10}H_8$, is a well known pest repellant and is probably best known as a moth repellant. Naphthalene is virtually insoluble in water and volatilizes over a period of time into the atmosphere. However, naphthalene is relatively harmless to the environment when compared to conventional pesticides.

In one embodiment of the invention, naphthalene is dissolved in alcohol and is injected and stirred into the soil. The naphthalene will precipitate after injection and will volatilize into the soil and repel nematodes and other soil pathogens. The amount of naphthalene applied per acre will vary depending on the length of time one wishes to maintain control. The more rapid the volatilization occurs, the more naphthalene will be used. In practice, when naphthalene is injected into or upon the surface of the soil, a range of one (1) lb to one thousand (1000) lbs. per acre will be used.

A solution of naphthalene and alcohol will precipitate in the soil and will volatilize quickly thereby requiring a larger amount to be used per acre. The subsurface tools disclosed in my U.S. Pat. No. 5,259,327 may be used to inject the naphthalene solution into the ground.

In another embodiment of the invention, naphthalene was first partially solubilized in a solubilizing agent such as alcohol or a suitable solvent. The partially solubilized naphthalene is then precipitated in an aqueous solution to produce a fine flocculent state. This flocculent naphthalene will then be injected into the soil with subsurface tools in the manner of the first embodiment. Since the naphthalene is in a fine flocculent state, it will therefore persist longer before completely volatilizing.

In another embodiment of the invention, naphthalene flocculents are first produced, for example in the manner of the second embodiment described hereinabove, and the flocculents are then micro-encapsulated in well known polymers such as methylacrylate, starch, synthetic acrylates, oils, saran, etc. The micro-encapsulated naphthalene flocculents are then injected into the soil in the manner in the embodiments described hereinabove so as to release the naphthalene vapors over a longer period of time compared to the previously mentioned embodiments. In the encapsulated condition, the naphthalene flocculents persist over a longer period of time and thereby requiring a lesser amount of naphthalene. It is pointed out that the naphthalene used in the methods of all of these embodiments will be distributed evenly within the soil or upon the surface thereof for the purpose of allowing the naphthalene to volatilize over a set pre-determined period of time.

In a further embodiment of the invention, the naphthalene flocculents can be incorporated in or attached to carriers such as cotton, rayon, wool, nylon, plastic or paper or such carriers. The carriers may then be advantageously placed in the soil where the naphthalene flocculents will volatilize and repel nematodes and other soil pathogens. The carriers may be placed as a mulch on top of the soil and will volatilize and repel nematodes and other pathogens.

The carrier strips may also be attached to trees or growing plants and the volatilizing naphthalene flocculents will repel noxious insects and insect larvae. When the naphthalene flocculents are embedded or attached to plastic, nylon, paper or similar carrier materials, the naphthalene will be micron-size and the strips or carrier will be shaped and formed to be readily applied to trees and plants without damage thereto. For example, the strips may be attached to fruit trees to protect the fruit from insects and insect larvae. When the micron-sized naphthalene particles are secured to carriers, a lessor amount of the naphthalene will be used. It has been found that a range of one tenth of one pound to five hundred (500) lbs. per acre is adequate when using the material as a mulch or strips of bedding into the soil.

From the aforegoing description, it will be seen that I have provided a novel method of controlling soil and plant pests by means which are relatively harmless to the environment compared to conventional pesticides.

What is claimed is:

1. A method of repelling pests comprising, applying strips of carrier material to trees or plants, the carrier material having naphthalene flocculate capsules attached thereto, the flocculated naphthalene being encapsulated in a polymer material selected from the group consisting of methyl acrylate, starch, synthetic acrylates, and saran, the carrier strips comprising plastic or paper material, nylon, or cotton, the naphthalene flocculate capsules slowly volatilizing to repel pests.

2. The method as defined in claim 1 wherein said pests are insects or insect larvae.

* * * * *